United States Patent
Bohme et al.

(12)

(10) Patent No.: US 6,245,791 B1
(45) Date of Patent: Jun. 12, 2001

(54) USE OF 2-AMINO-6-TRIFLUOROMETHOXYBENZOTHIAZOLE FOR THE PREVENTION OR TREATMENT OF CEREBELLAR DYSFUNCTION

(75) Inventors: Andrees Bohme, Paris; Alain Boireau, Sucy en Brie; Thierry Canton, Etrechy; Assunta Imperato, Saint Cloud, all of (FR)

(73) Assignee: Aventis Pharma S.A., Antöny (FR)

( * ) Notice: Subject to any disclaimer, the term of this patent is extended or adjusted under 35 U.S.C. 154(b) by 0 days.

(21) Appl. No.: 09/631,798

(22) Filed: Aug. 3, 2000

Related U.S. Application Data

(63) Continuation of application No. PCT/FR99/00230, filed on Feb. 3, 1999.

(30) Foreign Application Priority Data

Feb. 6, 1998 (FR) .................................. 98/01402

(51) Int. Cl.⁷ ................................................ A61K 31/425
(52) U.S. Cl. ............................................. 514/367
(58) Field of Search .............................. 514/367

(56) References Cited

U.S. PATENT DOCUMENTS 5,624,945 * 4/1997 Bousseau et al. .................. 514/367
5,674,885 * 10/1997 Boireau et al. ..................... 514/367
5,686,475 * 11/1997 Delumeau et al. .................. 514/367

OTHER PUBLICATIONS

Doble; The pharmacology and mechanism of action of riluzole, Neurology 47(Suppl 4):S233–S241 (Dec. 1996).
Dessi et al., Riluzole prevent anoxic injury in cultured cerebellar granular neurons, European Journal of Pharmacology 250:325–328 (1993).
Debondo et al., Electrophysiological studies of the effects of Riluzole on Purkinje Cells in Cerebellar Slices, BR. J. Pharmacol. 97:584 (1989).

* cited by examiner

*Primary Examiner*—Raymond Henley, III

(57) ABSTRACT

A method for the prevention or treatment of cerebellar dysfunction, particularly cerebellar ataxia, by the use of riluzole or a pharmaceutically acceptable salt thereof.

6 Claims, 1 Drawing Sheet

USE OF 2-AMINO-6-TRIFLUOROMETHOXYBENZOTHIAZOLE FOR THE PREVENTION OR TREATMENT OF CEREBELLAR DYSFUNCTION

RELATED APPLICATIONS

This application is a continuation of PCT/FR99/00230, filed Feb. 3, 1999, which claims priority from French Application No. FR98/01402, filed Feb. 6, 1998.

FIELD OF THE INVENTION

The present invention relates to a new therapeutic use of 2-amino-6-trifluoromethoxybenzothiazole known under the international non-proprietary name "riluzole" or a pharmaceutically acceptable salt of this compound.

BACKGROUND OF THE INVENTION

Riluzole is marketed for the treatment of amyotrophic lateral sclerosis. This compound is also useful as an anticonvulsant, an anxiolytic and a hypnotic (EP50551), in the treatment of schizophrenia (EP305276), in the treatment of sleep disorders and of depression (EP305277), in the treatment of cerebrovascular disorders and as an anaesthetic (EP282971), in the treatment of spinal, cranial or craniospinal traumas (WO94/13288), as a radio restorative (WO94/15600), in the treatment of Parkinson's disease (WO94/15601), in the treatment of neuroAIDS (WO94/20103), and in the treatment of mitochondrial diseases (WO95/19170).

Glutamate is one of the most widespread and most important neurotransmitters of the nervous system. Its effects on the neurons are modulated by transport proteins which cause glutamate to penetrate inside cells. The molecular structure of four glutamate transporters is well known (Gegelashvili, G. and Schousboe, A., *J. Pharmacol. Exp. Ther.*, 52: 6–15, 1997; Takahashi, M. et al., *J. Exp. Biol.*, 200: 401–409, 1997) and a fifth transporter has been recently identified (Arriza, J. L., et al., *Proc. Natl. Acad. Sci. USA*, 94: 4155–4160). Methods of histological localization indicate that these transporters are not all uniformly present in the various types of cells encountered in the nervous system. Two of the first transporters identified, called GLAST (or EAAT1) and GLT-1 (or EAAT-2), are predominantly located in the glial cells. The transporter EAAC-1 (EAAT-3) is expressed by the neurons through the whole brain. The transporter EAAT-4, more recently identified, is mainly expressed by a specific type of cerebellar neurons called Purkinje cells (Nagao, S., et al., *Neurosciences*, 78: 929–933, 1997). The most recently identified transporter is called EAAT-5 and is found in the retina of the eye.

The Purkinje cells use gamma-aminobutyric acid (GABA) as neurotransmitter. Glutamate being a metabolic precursor of GABA (*Biochemistry and the Central Nervous System*, McIlwain, H. M., and Bachelard, H. S. (eds.), Churchill Livingston, London, 1971, p. 193), one of the roles of the transporter EAAT-4 would be to participate in the supply of glutamate to the cerebellar Purkinje cells in order to ensure the synthesis of their neurotransmitter. This is corroborated by recent studies which show that the loss of the transporter EAAT-4, unlike that of the transporters EAAT-1, EAAT-2 and EAAT-3, causes cerebellar dysfunction which causes ataxia-type behavioral symptoms in rodents (Maragakis, N., et al., Soc. Neurosci. Abstr., 23: 1484, 1997).

DESCRIPTION OF THE INVENTION

Figure 1:
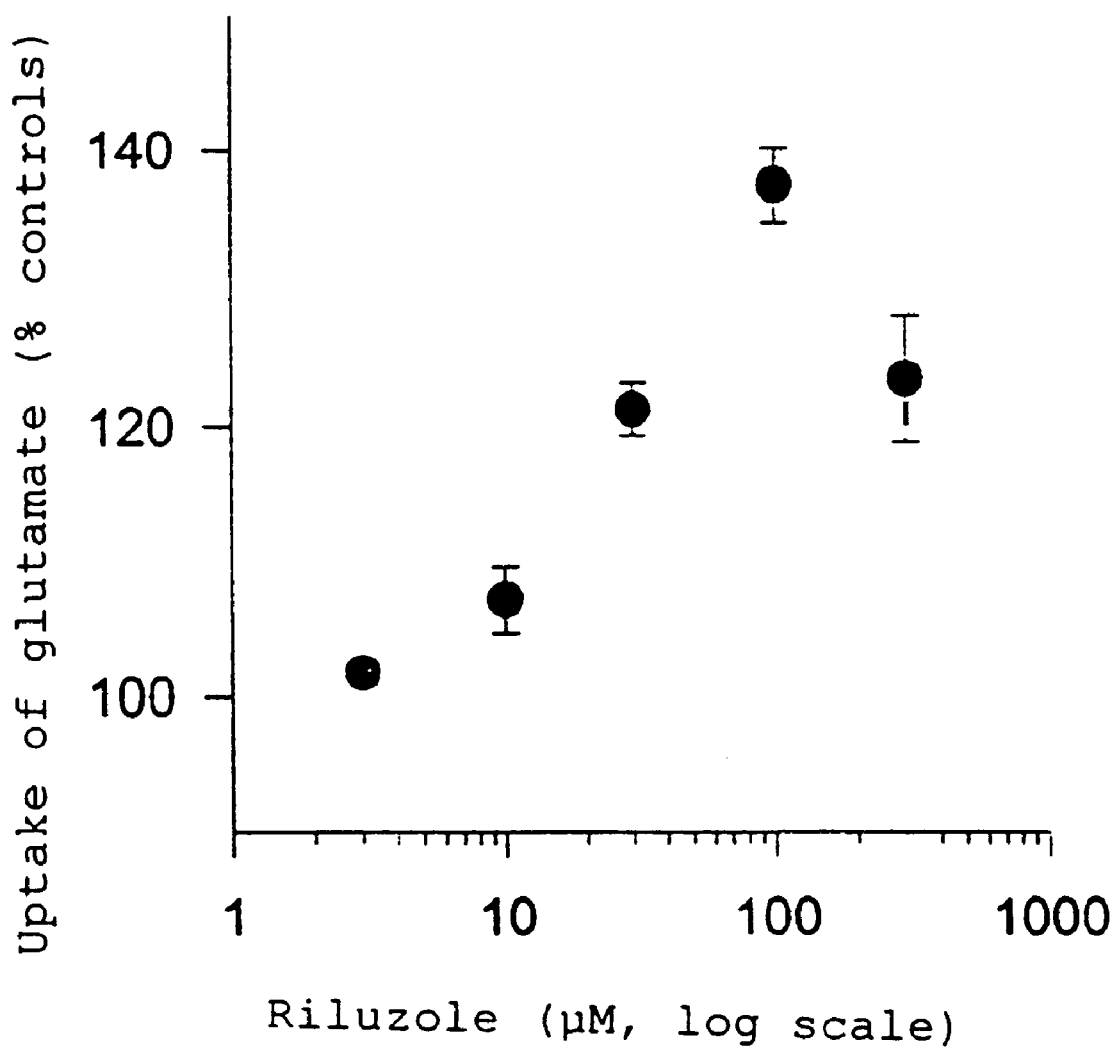
FIG. 1 is a graph that represents the uptake of radio-labelled glutamate in the synaptosomes of rat cerebellum (y-axis) as a function of increasing concentrations of riluzole (x-axis), thus showing the increase in the transport of glutamate in the cerebellum by the use of riluzole.

It has now been found, surprisingly, that riluzole stimulates the transport of glutamate in rat cerebellar preparations. Thus, riluzole can be used for the prevention or treatment of cerebellar dysfunction, especially that due to a poor supply of glutamate to the cerebellar cells. Cerebellar ataxia may be mentioned among these types of dysfunction.

This effect is specific to the cerebellum because it is not observed with similar preparations prepared from other brain structures such as the cerebral cortex and the striatum, or from the spinal cord. Moreover, the increase in glutamate uptake in the cerebellum by riluzole increases with the age of the rats from the postnatal period to adult age, becoming stable after about 10 weeks, but strictly above a 350 g weight.

The increase in glutamate uptake is evaluated in a suspension of synaptosomes prepared from rat cerebellar cells. This type of preparation is known to allow the in vitro study of glutamate transport across the cell wall (Kanai et al., *Trends Neurosci.*, 16: 365–370, 1993).

In rat cerebellar synaptosomes, the uptake of radioactive glutamate is increased in a concentration-dependent manner by the addition of riluzole to these preparations (FIG. 1).

The synaptosomes were prepared according to a modification of the method described by Robinson, M. B., et al., (*Brain Res.*, 544: 196–202, 1991). The tissues of cerebellum or of other regions of the brain of male rats of the Sprague-Dawley breed are homogenized in a sucrose solution (0.32 M) at 4° C. and then centrifuged at 800 g for 10 minutes. The supernatant is then recentrifuged at 20,000 g for 20 minutes. The centrifugation pellet obtained is resuspended in an identical sucrose solution and then centrifuged again at 20,000 g for 20 minutes. The synaptosomes are contained in this second centrifugation pellet. They are suspended and used immediately for measuring glutamate uptake. This is monitored with the aid of tritium-labelled glutamate ([$^3$H] glutamate) diluted in a solution of nonradioactive glutamate. After 3 minutes of incubation at 37° C., the synaptosomes are separated from the incubation medium by filtration. The effect of the product is evaluated by comparing the radioactivity retained by the filters in the absence or in the presence of increasing concentrations of riluzole at pH 7.3. This radioactivity is proportional to the glutamate uptake. The results are expressed as specific uptake, that is to say the uptake which depends on the presence of sodium ions in the incubation medium. It can be distinguished from the non-specific uptake which corresponds to the radioactivity measured after equimolar replacement of sodium chloride in the incubation medium with choline chloride. The specific uptake corresponds to the total radioactivity minus the radioactivity measured in the presence of choline chloride.

FIG. 1 shows the increase in the transport of glutamate in the cerebellum by the use of riluzole. The graph represents the uptake of radio-labelled glutamate in the synaptosomes of rat cerebellum (y-axis) as a function of increasing concentrations of riluzole (x-axis). The data are the mean values±SEM of n=8 independent observations. The maximum increase in uptake observed in the presence of riluzole reaches nearly 40% of the control values. The half-maximum effective concentration ($EC_{50}$) of riluzole in this experimental series, calculated by sigmoidal regression, stands at 24.5 μM.

As pharmaceutically acceptable salts of riluzole, there may be mentioned especially the addition salts with inorganic acids such as hydrochloride, sulfate, nitrate or phosphate, or organic acids such as acetate, propionate, succinate, oxalate, benzoate, fumarate, maleate, methanesulfonate, isethionate, theophyllineacetate, salicylate, phenolphthalinate, methylenebis-β-oxynaphthoate or substitution derivatives of these derivatives.

The medicaments consist of at least riluzole in free form or in the form of an addition salt with a pharmaceutically acceptable acid, in a pure state or in the form of a composition in which it is combined with any other pharmaceutically compatible product, which may be inert or physiologically active. The medicaments according to the invention may be used by the oral, parenteral or rectal route.

As solid compositions for oral administration, tablets, pills, powders, (gelatin capsules, cachets) or granules may be used. In these compositions the active ingredient according to the invention is mixed with one or more inert diluents such as starch, cellulose, sucrose, lactose or silica, under an argon stream. These compositions may also comprise substances other than diluents, for example one or more lubricants such as magnesium stearate or talc, a coloring, a coating (sugar-coated tablets) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The sterile compositions for parenteral administration may preferably be solutions which are aqueous or nonaqueous, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. The sterilization may be carried out in several ways, for example by aseptisizing filtration, by incorporating sterilizing agents into the composition, by irradiation or by heating. They can also be prepared in the form of sterile solid compositions which can be dissolved at the time of use in sterile water or in any other injectable sterile medium.

The compositions for rectal administration are suppositories or rectal capsules which contain, in addition to the active product, excipients such as cocoa butter, semisynthetic glycerides or polyethylene glycols.

The doses depend on the desired effect, the duration of the treatment and the route of administration used; they are generally between 50 and 400 mg per day by the oral route for an adult with unit doses ranging from 25 to 200 mg of active substance.

In general, the doctor will determine the appropriate dosage according to the age, weight and all the other factors specific to the subject to be treated.

The following examples illustrate medicaments according to the invention:

EXAMPLE A

Tablets containing a 50 mg dose of active product having the following composition are prepared according to the usual technique:

| | |
|---|---|
| 2-Amino-6-trifluoromethoxybenzothiazole | 50 mg |
| Mannitol | 64 mg |
| Microcrystalline cellulose | 50 mg |
| Polyvidone excipient | 12 mg |
| Sodium carboxymethylstarch | 16 mg |
| Talc | 4 mg |
| Magnesium stearate | 2 mg |
| Anhydrous colloidal silica | 2 mg |
| Mixture of methylhydroxypropylcellulose, polyethylene glycol 6000, titanium dioxide (72:3.5:24.5) | |
| qs 1 finished film-coated tablet weighing 245 g | |

EXAMPLE B

Gelatin capsules containing a 50 mg dose of active product having the following composition are prepared according to the usual technique:

| | |
|---|---|
| 2-Amino-6-trifluoromethoxybenzothiazole | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE C

An injectable solution containing 10 mg of active product having the following composition is prepared:

| | |
|---|---|
| 2-Amino-6-trifluoromethoxybenzothiazole | 10 mg |
| Benzoic acid | 80 mg |
| Benzyl alcohol | 0.06 cm$^3$ |
| Sodium benzoate | 80 mg |
| Ethanol at 95% | 0.4 cm$^3$ |
| Sodium hydroxide | 24 mg |
| Propylene glycol | 1.6 cm$^3$ |
| Water | qs 4 cm$^3$ |

The invention also relates to the process of preparing medicaments useful in the prevention or treatment of cerebellar dysfunction, especially that due to a poor supply of glutamate to cerebellar cells and, in particular to the prevention or treatment of cerebellar ataxia, consisting in mixing riluzole or the pharmaceutically acceptable salts of this compound with one or more compatible and pharmaceutically acceptable diluents and/or adjuvants.

The invention also relates to the method for the prevention or treatment of cerebellar dysfunction, especially that due to a poor supply of glutamate to the cerebellar cells and, in particular to the prevention or treatment of cerebellar ataxia in humans, consisting in administering riluzole or one of its pharmaceutically acceptable salts to the patient.

What is claimed is:

1. A method for the prevention or treatment of cerebellar dysfunction in a patient, said method comprising administering to said patient an effective amount of riluzole or a pharmaceutically acceptable salt thereof.

2. The method of claim 1 wherein said cerebellar dysfunction is due to a poor supply of glutamate to the cerebellar cells.

3. The method of claim 1 wherein said cerebellar dysfunction is cerebellar ataxia.

4. The method of claim 2 wherein said cerebellar dysfunction is cerebellar ataxia.

5. The method of claim 1 wherein said effective amount comprises 50 to 400 mg per day.

6. The method of claim 1 wherein said effective amount comprises 25 to 200 mg per unit dose.

\* \* \* \* \*